US012329722B2

(12) United States Patent
Kondakov et al.

(10) Patent No.: US 12,329,722 B2
(45) Date of Patent: Jun. 17, 2025

(54) FINISHED PHARMACEUTICAL FORM WITH INDIVIDUAL MEDICINE DOSING CAPABILITY (EMBODIMENTS) AND METHODS OF ITS PRODUCTION AND USE

(71) Applicant: PSIMOS, INC., New Canaan, CT (US)

(72) Inventors: Sergey Emilevich Kondakov, Moscow (RU); Aleksandr Pavlovich Osipov, Moscow (RU); Mikhail Yakovlevich Melnikov, Moscow (RU); Dmitry Mikhailovich Mikhailov, Moscow (RU); Maxim Yurievich Mitrohin, Moscow (RU); Sergey Olegovich Belezkii, Moscow (RU); Vladimir Vladimirovich Gordeev, Moscow (RU)

(73) Assignee: PSIMOS, INC., New Canaan, CT (US)

( * ) Notice: Subject to any disclaimer, the term of this patent is extended or adjusted under 35 U.S.C. 154(b) by 1064 days.

(21) Appl. No.: 17/122,266

(22) Filed: Dec. 15, 2020

(65) Prior Publication Data

US 2021/0093512 A1    Apr. 1, 2021

Related U.S. Application Data

(63) Continuation-in-part of application No. 16/345,448, filed as application No. PCT/RU2017/000482 on Jul. 3, 2017, now Pat. No. 10,898,447.

(30) Foreign Application Priority Data

Oct. 27, 2016  (RU) ................................ 2016142022
Feb. 27, 2017  (RU) ................................ 2017106044

(51) Int. Cl.
*A61J 3/07*  (2006.01)
*A61J 3/00*  (2006.01)
(Continued)

(52) U.S. Cl.
CPC ............... *A61J 3/078* (2013.01); *A61J 3/002* (2013.01); *A61K 9/70* (2013.01); *A61K 45/06* (2013.01);
(Continued)

(58) Field of Classification Search
CPC ............. A61J 3/002; A61J 3/078; A61K 9/70; A61K 45/06; A61M 35/10; A61M 2207/10; B41J 11/002; B41J 2202/01
See application file for complete search history.

(56) References Cited

U.S. PATENT DOCUMENTS 4,712,460 A * 12/1987 Allen .................... A61J 7/0076
                                                        424/443
6,660,103 B1 * 12/2003 Johnston .............. B41J 2/16552
                                                        134/22.12
(Continued)

FOREIGN PATENT DOCUMENTS

RU    2519670 C2    12/2011
RU    2501395 C1    12/2013
(Continued)

OTHER PUBLICATIONS

Voura et al; "Printable medicines: A microdosing device for producing personalised medicines", Pharmaceutical Technology Europe, Jan. 2011, pp. 32-36. (Year: 2011).*

(Continued)

*Primary Examiner* — Charles S Bushey
(74) *Attorney, Agent, or Firm* — Buckley, Maschoff & Talwalkar LLC

(57) ABSTRACT

According to some embodiments, a method and system are provided including receiving a first quantity of at least one medicine in at least one cartridge of a plurality of cartridges of a printing device; receiving a porous media in the printing device; dispensing a first drop of the at least one medicine (Continued)

onto the porous media; and drying the dispensed drop on the porous media. Numerous other aspects are provided.

16 Claims, 4 Drawing Sheets

(51) Int. Cl.
   *A61K 9/70* (2006.01)
   *A61K 45/06* (2006.01)
   *A61M 35/00* (2006.01)
   *B41J 11/00* (2006.01)

(52) U.S. Cl.
   CPC ............ *A61M 35/10* (2019.05); *B41J 11/002* (2013.01); *A61M 2207/10* (2013.01); *B41J 2202/01* (2013.01)

(56) References Cited

U.S. PATENT DOCUMENTS

| | | | |
|---|---|---|---|
| 10,507,166 B2 | 12/2019 | Heo et al. | |
| 10,898,447 B2* | 1/2021 | Kondakov | A61K 9/7007 |
| 2005/0233000 A1* | 10/2005 | Figueroa | A61K 9/2893 |
| | | | 424/489 |
| 2010/0053254 A1* | 3/2010 | Ito | B41J 11/007 |
| | | | 347/19 |
| 2012/0225100 A1* | 9/2012 | Darcy | A61K 9/0056 |
| | | | 514/289 |
| 2016/0101108 A1* | 4/2016 | Sandler | A23L 33/15 |
| | | | 424/692 |
| 2016/0271367 A1 | 9/2016 | Hyde et al. | |
| 2019/0247319 A1 | 8/2019 | Kondakov et al. | |
| 2019/0282459 A1 | 9/2019 | Boswell et al. | |

FOREIGN PATENT DOCUMENTS

| | | |
|---|---|---|
| WO | 2014/039378 A1 | 3/2014 |
| WO | 2014188079 A1 | 11/2014 |
| WO | 2020237123 A2 | 11/2020 |

OTHER PUBLICATIONS

Genina et al; "Tailoring controlled-release oral dosage forms by combining inkjet and flexographic printing techniques", European Journal of Pharmaceutical Sciences, Aug. 2012, vol. 47, pp. 615-623. (Year: 2012).*

International Search Report and Written Opinion dated Mar. 8, 2022 which was issued in connection with a counterpart application PCT Application No. PCT/US21/72795.

* cited by examiner

FINISHED PHARMACEUTICAL FORM WITH INDIVIDUAL MEDICINE DOSING CAPABILITY (EMBODIMENTS) AND METHODS OF ITS PRODUCTION AND USE

The present application is a continuation-in-part and claims priority from the following U.S. Patent Application, which is hereby incorporated by reference herein in its entirety for all purposes:

U.S. patent application Ser. No. 16/345,448, filed Apr. 26, 2019, issued as U.S. patent Ser. No. 10/898,447 B2 on Jan. 26, 2021, and entitled "FINISHED PHARMACEUTICAL FORM WITH INDIVIDUAL MEDICINE DOSING CAPABILITY (EMBODIMENTS) AND METHODS OF ITS PRODUCTION AND USE".

This invention relates to medical science and pharmaceutical technology.

In accordance with the applicable definition, a pharmaceutical form is an artificially attained condition of a medicine or a herbal medical raw material that makes it suitable for administering and provides for the required therapeutical effect (Order of the Ministry of Health of the Russian Federation No. 82 as of 29 Feb. 2000, "Implementation of the Industrial Standard on the Quality Standards for Medicines. Basic Provisions"), or a condition of a medicine compliant with the methods of its introduction and administering and providing for the achievement of the required therapeutical effect (Federal Law of the Russian Federation No. 61-FZ as of 12 Apr. 2010 "Circulation of Medicines").

The following common classification is used for medicines: by pharmaceutical form, by aggregation form, by target and by method of administering.

By pharmaceutical form, medicines have the following classification:

undosed (unseparated): collections, medicinal pencils, skin glue, infusions, apozema, potions, elixirs and syrups;

dosed/undosed: powders, granules, ointments (including pastes, cremes, gels and liniments), plasters, suspensions, emulsions, solutions, mixtures and aerosols (including sprays);

dosed (separated): briquettes, capsules (including spansules and pellets), pills (including coated pills, glossettes and medicinal chewing gums), pellets, candies, pastilles, eye films, transdermal therapeutic systems, suppositories (including sticks, pessaries, and balls) and drops.

By aggregation form, medicines have the following classification:

hard: collections, medicinal pencils, powders, granules, briquettes, capsules (including spansules and pellets), pills (including coated pills and glossettes), pellets, medicinal chewing gums, marmalade etc., candies, pastilles and eye films;

soft: including pastes, cremes, gels and liniments), suppositories (including sticks, pessaries, and balls) and plasters (including transdermal therapeutic systems);

liquid: infusions, apozema, potions, elixirs, syrups (including drops), suspensions, emulsions and mixtures;

gaseous: aerosols (including sprays);

solid, soft or liquid: extractions including liquid extractions, thick extractions, dry extractions By target and method of administering, medicines have the following classification:

local;
general (systematic or resorptive);
enteral;
parenteral (including injection pharmaceutical forms, i.e. powders, suspensions, emulsions, solutions, orodispersive or sublingual pharmaceutical forms).

Thus, no description is provided for a finished pharmaceutical form comprising a storage container and a membrane carrier the latter being membraneous material with the active pharmaceutical substance being applied thereupon with capability of resuspending to the solution upon submersion.

One of the most important tasks of medical science and pharmacology in the field of antibiotic therapy is the choice of individual medicine dosage. In fact, a common practice in the field is currently a strategy implying individual calculation of adequate antibacterial medicine dosage based on a profound consideration of individual patient characteristics, e.g. weight, gender, renal function quality etc. with the use of specialized computer software.

Similar problems associated with the choice of individual medicine dosage are common to almost every field of medical science, including gynecology, cardiology, urology, anesthesiology etc., especially in intensive care departments.

Pharmacology experts nowadays increasingly tend to the opinion that in the nearest future pharmacological factories will have to master the production of medicines in new pharmaceutical forms as are suitable for new therapeutic strategies and individual dosage approach for this problem is becoming increasingly pressing, especially in intensive care departments and stationary healthcare facilities that do not have or are not permitted to have in-house compounding pharmacies or pharmacological departments.

Therefore the object of this invention is providing a finished pharmaceutical form allowing, in the course of its administering, for fast delivery of individual medicine dosage in the form of a peroral solution without the necessity of using any additional dosing devices or technical metering means, and furthermore providing a simple method of its production.

Known is (RU Patent 2519670, published 20 Jun. 2014) a pharmaceutical form having the form of edible soft chewing medicine.

Disadvantage of that technical solution is the limited application range of the respective pharmaceutical form, e.g. for cattle and poultry in agriculture, and furthermore this finished pharmaceutical form is not suitable for individual medicine dosing.

Known is (RU Patent 2501395, published 27 Jun. 2014) a pharmaceutical form, said form being an implant containing an active medicinal substance. The implant is made from a polymer material serving as a matrix in which the medicine is distributed. The implant may have any arbitrary shape, e.g., a rod, and is based on a biologically degradable polymer.

Disadvantage of that invention is the necessity of using complex process equipment for achieving a homogeneous distribution of the active medicinal substance in the copolymer and the impossibility of individual medicine dosing, because the active substance is released into the solution during a long time thus making it impossible to control its concentration at any specific time.

Known is (PCT/US2013/057466 Aug. 30, 2013) a method of producing a finished pharmaceutical form with the use of a known device, i.e. a printer. In accordance with the known method of producing a finished pharmaceutical form, a 3D printer is used for printing differently sized peroral pills thus providing for individual medicine dosing.

Disadvantage of that invention is the necessity of the initial provision of a composition containing the active substance of the medicine and the media substance, the latter having strictly predetermined characteristics, i.e. melting and solidification points, for its use in a 3D printer, this greatly reducing the potential application range.

The closest counterpart of the technical solution provided herein is (WO/2014/188079 Apr. 14, 2016) a method of producing finished personified pharmaceutical form with the use of a known device, i.e. a jet printer, wherein the finished peroral pharmaceutical form of vitamins, mineral additives and/or nicotinic acid is produced with the use of a jet printer allowing applying the solutions of vitamins and/or nicotinic acid on powders of mineral additives, further wherein individual dosage is provided by dosing the quantity of powder intended for peroral administration.

Disadvantages of that invention are the necessity of modifying the original design of a jet printer for achieving homogeneous application of the active substance on the powder, the necessity of using only powders that are allowed for peroral administration and the impossibility of obtaining individual powder dosage without applying additional dosing devices or technical metering means.

DETAILED DESCRIPTION

Figure 1:
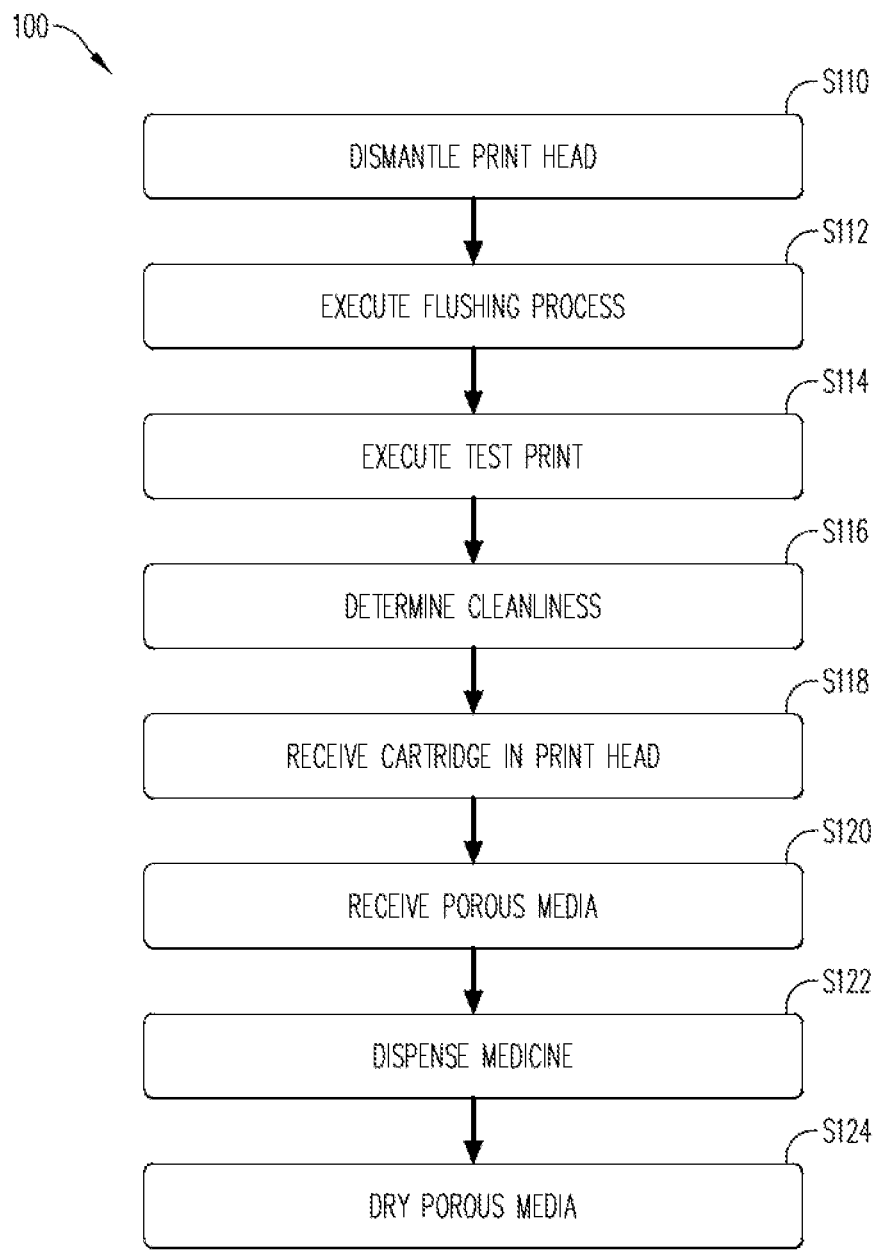
FIG. 1 is a flow diagram according to some embodiments.

The technical task solved by this invention is to provide a finished pharmaceutical form allowing, in the course of its application, for fast delivery of individual medicine dosage in the form of a peroral solution without the necessity of applying any additional dosing devices or technical metering means, and providing a simple method of its production. The technical task solved by this invention is also to provide a process for forming the finished pharmaceutical form, as well as an apparatus for forming the finished pharmaceutical form.

The technical result achieved by implementing this invention includes simplifying the technology of pharmaceutical production, broadening the range of applicable medicines and providing the possibility of producing finished pharmaceutical forms having novel consumer properties.

It is suggested to achieve the abovementioned technical result by using the technical solution provided herein.

The technical solution provided herein characterizes the first embodiment of the finished pharmaceutical form for individual medicine dosing in accordance with this invention, the latter being in the form of a water-insoluble porous media wherein said porous media is selected such as to provide for the quantity desorption capability of the medicine applied onto said media using a jet printer.

As used herein, the term "medicine" and "biologically active substance" may be used interchangeably. Non-exhaustive examples of medicine include: a vitamin, an antibiotic, an anti-viral substance, dietary supplement, anti-inflammatory drug, metabolite, anti-tumor oral drug, diagnostical contrast oral substance, nootripic, medical psychotherapeutic drug.

The use of porous media is dictated by the aim to increase the area of the surface capable of adsorbing the medicine by increasing the total surface area of pores.

In some embodiments of this invention the surface of said porous media is provided such as to allow fragmentation. To this end the surface of said porous media is provided with marking lines that divide the surface of said membrane media into fragments, or the surface of said porous media is provided with perforations that divide the surface of said membrane media into fragments.

Preferably, said medicine is homogeneously applied onto the media.

Preferably, said porous media has a preset desorption coefficient for the medicine being applied onto it, in order to allow applying medicines onto membrane media taking into account water desorption losses.

The inventors note that the deposition accuracy may be influenced by the stability of the desorption of the deposited medicine when the porous media is immersed in a solution. Non-exhaustive examples of porous media include filter paper and rice paper.

In one or more embodiments, the porous media 206 may be an absorbent material acceptable in the food industry, and intended for direct oral use, including, but not limited to, filter paper, rice food paper, and other suitable edible paper. The porous media 206 may be an absorbent porous media that receives the dosed medicine and acts as a storage medium for the dosed medicine. From the porous media, the dosage of medicine is passed into a solution upon dissolution/stirring for further use as intended. The porous media may have a given porosity in a range of 0.2-0.85% and a hydrophilicity, measured by a drop angle, in a range of 35°-135°. Other suitable porosity and hydrophilicity may be used.

It is noted that, as compared to filter paper, for example, in most cases, the use of rice paper shows less desorption of the medicine in solution. The inventors note this may be due to the gelation of the rice paper when mixed with water and "locking" inside the gel some of the medicine that are not desorbed. It is noted that other suitable water-soluble porous media may be used, where the water-soluble porous media include less porosity than filter paper, and may not need drying after receiving a dosage of the medicine thereon. Typically, the storage container and/or the porous media has marking to show the dose of the medicine desorbed from unit area of said media to the solution taking into account desorption losses.

Preferably, tape-shaped porous media are used, said media being wrapped onto a holder wherein said holder and the media wrapped around it are placed with the capability of rotation into the storage container, further wherein the distal end of said membrane media extends outside said container.

Furthermore, the technical solution provided herein characterizes the second embodiment of the finished pharmaceutical form for individual medicine dosing in accordance with this invention. In accordance with the second embodiment of this invention, the finished pharmaceutical form is porous hydrophilic media containing the medicine immobilized in the membrane pores in a dry condition, obtained by preliminary introduction of a preset quantity of medicine into the pores of the media, followed by drying of the media, and capable of quantitative desorption to solution after porous media submersion into water. The pharmaceutical form provided herein contains medicine retained in the pores and possibly absorbed by the surface of the media, said medicine being capable of resuspending to the water phase, if necessary, as a result of the interaction of the porous media with water. The surface of the media can be hydrophilic due to the initial properties of the media material or due to its treatment with a hydrophilizing agent.

Along with immobilized medicine the surface of the porous media may further contain a coloring agent selected from coloring agents approved for use in the food industry. The color of the medicine and the coloring agent applied onto the surface of the media depend on the content of the medicine in order to allow color-based selection of the required medicine dosage. For example, medicine A is a different color than medicine B. In some embodiments, the color of the medicine may have a different color intensity based on the concentration of the dosage. For example, a 10 mg dosage may be a less intense (e.g., lighter) shade of green than a 100 mg dosage of the same medicine.

In some embodiments of the technical solution provided herein the porous media with medicine and, possibly, coloring agent applied onto its surface allows fragmentation. This provides for the possibility of accommodating multiple medicine dosages on a single piece of said media. The fragmentation capability of said porous media can be provided by dividing the surface of said porous media with special separation marking lines that delimit the fragments the porous media surface is divided into. Said marking lines on the surface of said porous media with immobilized medicine and coloring agent can be in the form of perforations that divide porous media fragments.

In the preferred embodiment of the finished pharmaceutical form provided herein said medicine and coloring agent are homogeneously applied onto said porous media.

Said medicine and coloring agent can be applied onto said porous media by submerging said porous media into a solution containing the required concentrations of the medicine and the coloring agent. Alternatively, said medicine and coloring agent can be applied onto said porous media by applying aliquot solutions of the medicine and the coloring agent on each of the individual fragments of the porous media using a jet printer, an automatic or a semiautomatic dosing device capable of operation with liquid pharmaceutical forms.

In the preferred embodiment of the invention said porous media has a pore size and a pore volume percentage allowing it to absorb and retain the required quantity of water solution within each individual fragment of porous media and, after drying, to quantitatively resuspend the dry active substance to the solution upon submersion of said fragment of porous media into water and subsequent exposure.

Typically, each medicine immobilized in the porous media is marked with an individual coloring agent having a specific color on the media and/or in water.

Different quantities of the same medicine immobilized in the porous media can be marked with individual coloring agents having specific colors on the media and/or in water. As noted above, in addition to the specific colors being different colors for different quantities, alternatively, the specific color may also be different intensities of a color. This will allow visually selecting the required quantity of medicine.

Said storage container and/or porous media show information on the dosage of medicine desorbed from each fragment of the porous media. The dose of medicine desorbed from each fragment of the porous media corresponds to a specific color or color intensity of the immobilized coloring agent.

In some embodiments of the invention said porous hydrophilic material can be water soluble. Said water soluble porous hydrophilic material can be selected, for example, from materials based on alginates or other natural polymers approved for use in the food or pharmaceutical industries.

In some embodiments of the invention said pharmaceutical form is capable, after drying, of reversibly and quantitatively resuspending the dry active substance and the fragment of the porous media to the solution upon submersion in water and subsequent exposure.

In some embodiments of the technical solution provided herein, thin porous media can be used, e.g. filtering membranes; although, relatively thick porous media can be used, e.g. unwoven pre-filters.

In some embodiments of the invention said porous media can be in the form of a narrow tape wrapped onto a rotating axial holder fastened in a container, the distal end of said tape extending outside said container to allow physical detachment of the delimited fragments. Sheet shaped media can be alternatively used.

In some embodiments of the finished pharmaceutical form provided herein, said finished pharmaceutical form additionally has marking made in a different color. Said marking may show auxiliary information, advertisement or other information.

Figure 4:
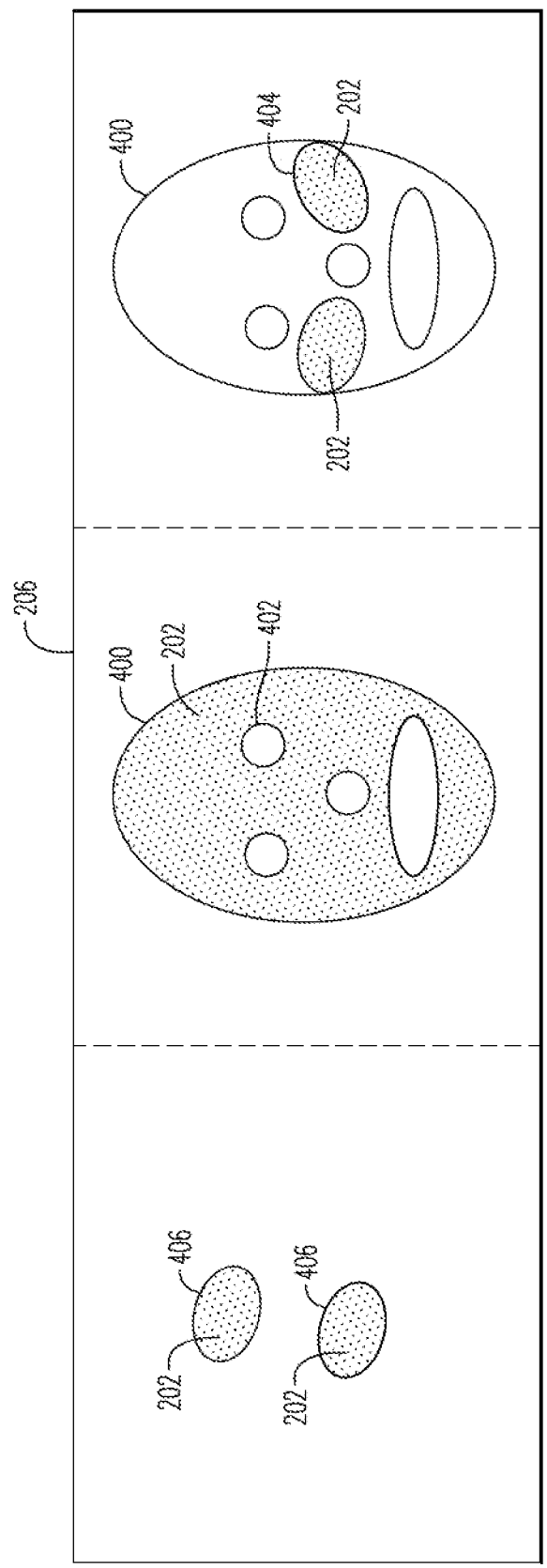
FIG. 4 is a non-exhaustive example of a facial sheet mask.

In some embodiments, one or more skin mask shapes 400 (FIG. 4) may be printed on the porous media. It is noted that while the skin mask shapes 400 in FIG. 4 are for a face, other suitable skin mask shapes may be used. For example, skin mask shapes 400 may be shaped as nails, hands, feet, neck, etc. The skin mask shape may be printed by the application of medicine to the porous media in a manner that forms a skin mask shape, or the skin mask shape may be pre-printed on the porous media prior to application of the medicine thereto. The skin mask shape may incorporate the dosage of medicine. As a non-exhaustive example, the skin mask shape for a hand may be administered to a user via adhesion thereof to a backside of a hand and may not prevent use of the hand while the hand receives the medicine (e.g., a user may still type, garden, etc. while wearing the skin mask shape 400). In the case of a skin mask shaped as a face, the skin mask may be referred to as a "face mask" or a "face mask sheet," and may be administered to a user via adhesion to the skin, or via other suitable delivery process. In some embodiments, the face mask shape may be for less than an entire face (e.g., a nose shape, cheek shapes 406, etc.). In some embodiments, the face mask shape may be shaped for an entire face, while the dosage of medicine may be included on less than the entire face mask (e.g., in one or more discrete regions 404). Similarly, other skin mask shapes may be shaped for less than an entire body part/area of skin or may be shaped for an entire body part/area of skin, while the dosage of medicine may be included on less than the entire skin mask shape. In one or more embodiments, multiple skin mask shapes may be included on the porous media. As described above, the surface of said porous media is provided with marking lines that divide the surface of said membrane media into fragments, delineating the multiple masks or the surface of said porous media is provided with perforations that divide the surface of said membrane media into fragments, with each fragment including a mask. The inventors note that by including the medicine in the porous media via the targeted process described herein, less active medicine may be used than with conventional facial sheet masks, for example, that are soaked in the medicine. A reason for this, which respect to conventional facial sheet masks, is that often a conventional facial sheet mask includes cut-out areas for a user's eyes, nose, etc., which may be removed by the user. However, these "cut-out" areas are soaked with the medicine during the manufacturing process. The embodiments described herein provide a process whereby a targeted area of the porous media receives the medicine so that there is no waste (i.e., removing the cut-outs). It is noted that in one or more embodiments, the cut-out areas 402 may be formed prior to application of the medicine to the surrounding face mask, or after application of the medicine to the surrounding face mask.

Furthermore, the technical solution provided herein characterizes the method of producing the finished pharmaceutical form for individual medicine dosing.

In accordance with the method provided herein, and as described further below with respect to FIGS. 1-3, the preliminarily prepared solution of the medicine is charged into the jet printer cartridges or into containers of any other automatic liquid media dosing device wherein the application of the medicine on the porous media is effected using said jet printer or other automatic liquid media dosing device, A further embodiment is available wherein said jet printer or other automatic liquid media dosing device is used for applying multiple active substances onto the porous media from different cartridges (containers).

The quantity of medicine applied onto said porous media can be controlled either by varying the concentration of the solution charged into jet printer cartridges, or by limiting the application time of solutions having the same concentration, or by software controlling the quantity of solution microdrops that are applied onto the unit surface area of the porous media.

Said porous media can be selected from materials based on cellulose or its modifications as well as paper or unwoven-materials based on glass, fiberglass, standard paper, specific printer paper, filter paper, edible rice paper, or polymer fibers or fibers produced from raw materials of vegetation origin (jutte, copra, leaf fiber, liana fiber, linen fiber etc.).

Figure 2:
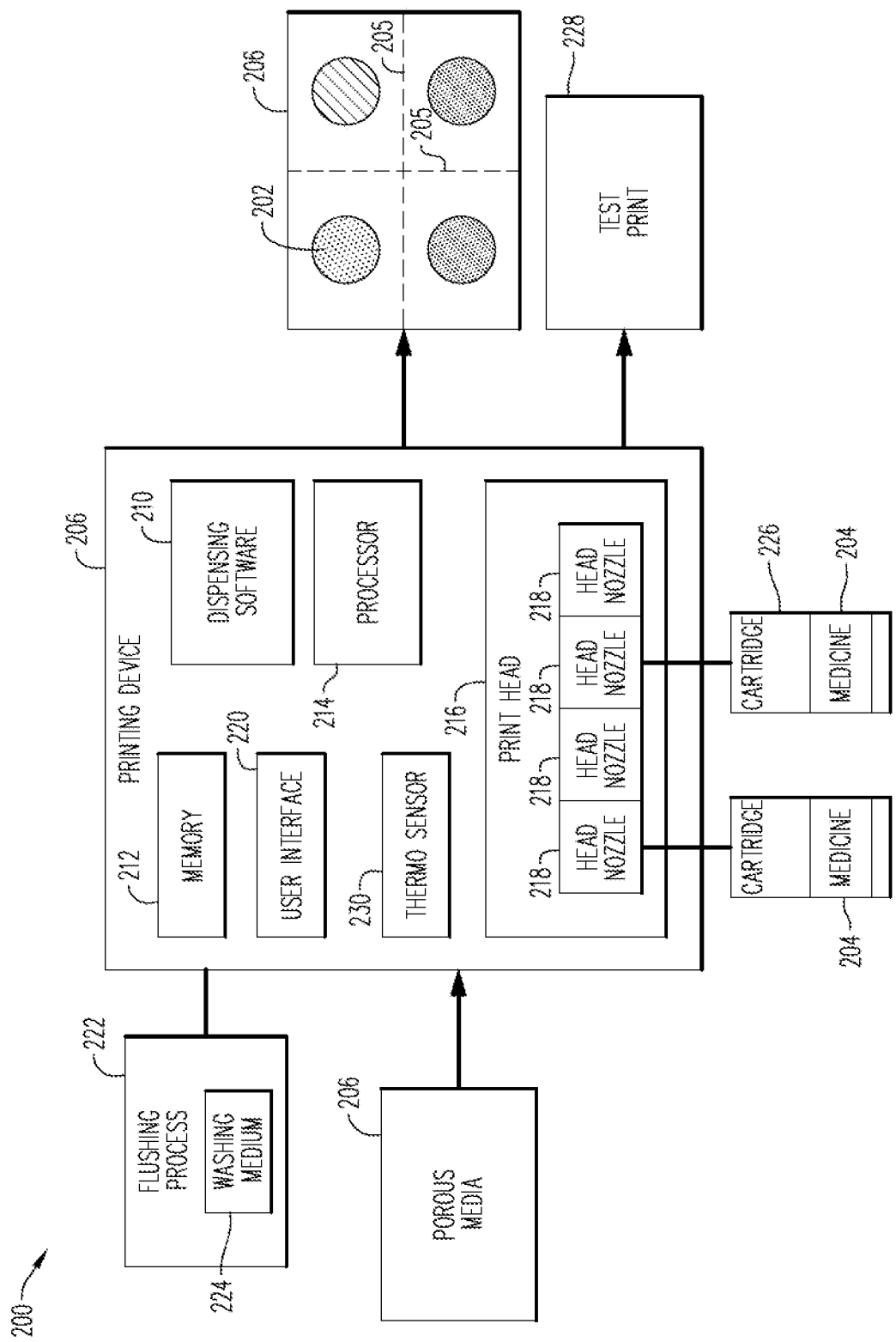
FIG. 2. is a block diagram of a system according to some embodiments.
Figure 3:
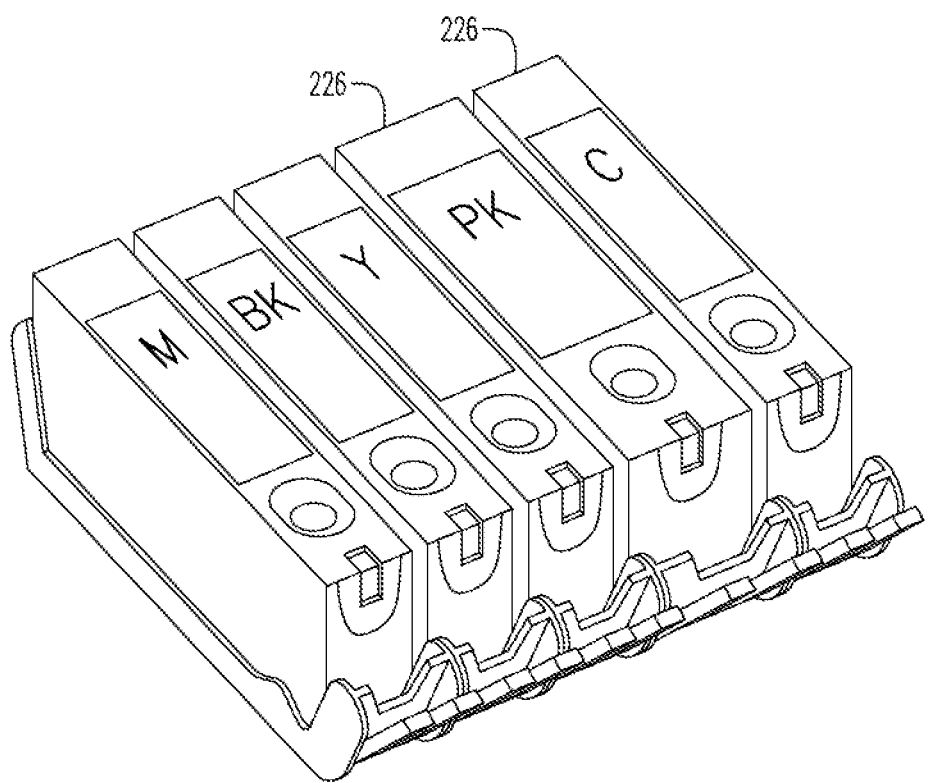
FIG. 3 is a plurality of cartridges according to some embodiments.

FIGS. 1 and 2 include a flow diagram of a process 100 and a system 200 for applying a drop 202 of medicine 204 onto a porous media 206 using an inkjet printer 208. As described further below, the drop 202 may be one of a first dose of medicine and a part of a first dose of medicine. Process 100 may be executed, in part, by software 210 according to some embodiments. In one or more embodiments, the software 210 may be conditioned to perform at least some of the process 100, such that a processor 214 of the system 200, used to execute the software 210, is a special purpose element configured to perform operations not performable by a general-purpose computer or device.

At least some of the processes mentioned herein may be executed by various hardware elements and/or embodied in processor-executable program code read from one or more of non-transitory computer-readable media, such as a hard drive, a floppy disk, a CD-ROM, a DVD-ROM, a Flash drive, Flash memory, a magnetic tape, and solid state Random Access Memory (RAM) or Read Only Memory (ROM) storage units, and then stored in a compressed, uncompiled and/or encrypted format. In some embodiments, hard-wired circuitry may be used in place of, or in combination with, program code for implementation of processes according to some embodiments. Embodiments are therefore not limited to any specific combination of hardware and software.

User interfaces 220 may be presented on any type of display apparatus (e.g., desktop monitor, smartphone display, tablet display) provided by any type of device (e.g., desktop system, smartphone, tablet computer).

Initially, at S110, a head 216 of a printing device 208 is dismantled. The head 216 of the printing device 208 may include a plurality of head nozzles 218 operative to dispense a liquid therefrom. The printing device 208 may be a piezoelectric apparatus, or any other suitable apparatus. The printing device 208 may accurately (e.g., within 5% of a nominal range) output a range of drop sizes (e.g., 2-80 picolitres) at a relatively high dispensing frequency (e.g., 1000-3000 drops per second). The printing device 208 may operate based on an inverse piezoelectric effect, whereby a piezoelectric element is deformed under the influence of an electric field. A benefit of using a piezoelectric apparatus is their ability to achieve high operating speeds that do not exceed overloads. In one or more embodiments, the printing device 208 may include a thermo sensor 230 to control the temperature of the head 216 to avoid heating the medicine to a temperature that results in decomposition of the medicine. In embodiments, the thermo sensor may be a thermistor temperature sensor, or other suitable heat sensor. In some embodiments, in a case that the thermo sensor detects overheating, the dosing process may be halted, and a fan, or other suitable cooling element cools the nozzle of the apparatus. In some embodiments, in a case that the thermo sensor detects overheating, a capillary cooling system is executed, and the dosing process may continue while the nozzle is cooled. The capillary cooling system may include a microfluidic chip attached to the printing apparatus (e.g., a bottom of the head—around the nozzle). It is noted that the ranges of acceptable temperatures may be analyzed, as cooling may affect viscosity of the medicine. As a non-exhaustive example, it may be desirable to have the viscosity of the medicine range from 0.4 to 25 cP. Other suitable values may be used. The inventors note that, per their research on the use of vitamin C in a piezoelectric apparatus, during application of the medicine to the porous media, heat resulting from the use of the piezoelectric apparatus occurred above 40 degrees Celsius, as vitamin C was destroyed and its presence was not detected during chromatography. In other words, during the printing process, a print head may become hot enough that it may reach a decomposition temperature for the medicine, and the medicine will decompose. To address this, one or more embodiments provide, as described above, introduction of additional substances, allowed in a given pharmacopeia, for modification of viscosity of a drug solution. In one of the embodiments antioxidants may be added to the solution for increased stability of the drug after dispensing.

Then in S112, a flushing process 222 is executed. The head 216 ("print head") of the printing device 208 may be washed with a washing medium 224 via the flushing process 222. The flushing process 222 may be executed manually or automatically. The washing medium 224 may be isopropyl alcohol, flushing liquid, or any other suitable washing medium that removes the residual amount of pharmaceutical substance. As part of the flushing process 222, the washing medium 224 may be poured directly into a plurality of the head nozzles 218. The washing medium 224 may be poured using a syringe (e.g., 20 ml), with the needle removed, or via any other suitable mechanism. It is noted that the cartridges 226 may include adsorption sponges or other medium as part of their structure. As a consequence of the adsorption medium, the pores thereof may be blocked by an aggregation of medicine that may oxidize thereon. To address this, some embodiments may apply the flushing process 222 to the cartridges, while other embodiments may employ cartridges that do not include the adsorption sponges. In one or more embodiments, as part of the flushing process 222, cartridges 226 may be filled with the washing medium 224, coupled to the print head 216, and the washing medium may be dispensed from the head nozzles. It is noted that the flushing process 222 of filling the cartridges with washing medium may be used in addition to, or instead of, applying the washing solution directly to the head nozzles.

Next, in S114, a test print 228 is executed. The test print 228 may be executed with clean food-grade ink, whereby the printing device 208 is executed, and food-grade ink is dispensed from the head nozzles. The test print 228 may be used to visually check the cleanliness of the head nozzles and/or cartridges. Then in S116 it is determined whether the head nozzles 218 and/or cartridges are clean. In one or more embodiments, the head nozzles 218 and/or cartridges are determined to be "clean" when liquid chromatography of used washing solution does not demonstrate peaks, characteristic for previously dispensed pharmaceutical substance, in concentrations up to $10^{-6}$ mol, or other suitable ranges.

Once the head nozzles and/or cartridges are clean, the cartridges are ready for receipt by the print head 216. At least one cartridge 226 (FIG. 2 and FIG. 3) of a plurality of cartridges including medicine 204 therein is received in the print head 216 in S118. It is noted that, in one or more embodiments, the process may begin with the receipt of at least one cartridge in the print head, without the dismantling and cleaning steps. Each cartridge may retain a quantity of medicine. In embodiments, a solution of the medicine is received in each cartridge. Alternatively, the cartridge 226 is pre-filled with the medicine. In embodiments where a user inserts the medicine into the cartridge, to prepare a vitamin solution, a weighted portion of a vitamin may be mixed with liquids including deionized water and at least one of phosphorus and sodium bicarbonate buffer solution. Depending on the dispensing substance, related buffer solutions are used. To buffer solutions, antioxidants and supplement substances can be added for modification of viscosity and density of the drug solution. Other suitable soluble solids, non-soluble suspensions and liquids may be added. It is also noted that a micellization process may be applied to non-soluble particles to make them hydrophilic, and then these processed particles may be added. This solution may be periodically shaken and subjected to an action of ultrasound until complete dissolution is achieved. It is noted that the phosphoric acid may improve the stability of the solutions of vitamins.

Then in S120, the porous media 206 is received by the printing device 208. In S122, the medicine is dispensed from the printing device 208 and applied to the porous media 206 via execution of the printing device 208. In one or more embodiments, the medicine may be dispensed as a drop 202 on the porous media 206. The drop 202 may be one of a complete first dose of the medicine or a part of a first dose of the medicine. In instances where the drop is part of the first dose, additional drops may be added to the first drop to form a complete dose of the medicine. It is noted that an array of drops may be used to provide a sufficient volume of a dose. In one or more embodiments, the drops and/or dosages may be separated by separation marking lines 205 on the porous media 206. In embodiments, the quantity of medicine dispensed on the porous media may be controlled by varying a concentration of the medicine. For example, one cartridge may include a first concentration of medicine, while another cartridge may include a second concentration of medicine. As another example, each drop of a first size may include 10 mg of medicine, and a drop of a second size may include 15 mg of medicine. As yet another example, multiple drops may increase the concentration of the medicine (e.g., each drop includes 10 mg of medicine), so adding a second drop to the first drop may increase the concentration. In embodiments, a quantity of medicine dispensed on the porous media 206 may be controlled by opening a piezoelectric element of a printer for various amounts of time, allowing varied amounts of liquid to pour therethrough. For example, increasing the time during which the piezoelectric element is open, the amount of dispensed substance is increased.

In some embodiments, a second cartridge may retain a quantity of a second medicine, and at least one drop of the second medicine may also be dispensed on the porous media 206. The drop of the second medicine may be dispensed at a same time as a drop of the first medicine, or at a different time. The first drop and the second drop may be spaced apart on the porous media by a pre-set amount. In one or more embodiments, the medicines may include individual coloring agents, each having a specific color. The specific color may be displayed on the porous media. For example, FIG. 2 shows drops having different shadings/patterns to represent different medicines. In particular, there are four drops, two of which are the same. In some embodiments, different colors or different color intensities (e.g., shade) may denote different concentrations of a same medicine. For example, in FIG. 2, the darker solid color circle may be the same medicine as the solid lighter color circle, but a different concentration, while the patterned color circle represents a different medicine than the solid color circles.

After the medicine is dispensed onto the porous media 206, the porous media is dried in S124. In one or more embodiments, the porous media 206 may be dried at room conditions (+20 C) at normal humidity.

In one or more embodiments, a dispensing software 210 may be used by the printing device 208 that allows a user to separately control the dispensing of the medicine from each cartridge 226. A non-exhaustive example of dispensing software is CorelDraw X 7 v. 17.6.0.1021. The dispensing software 210 may allow a user to control the number of working head nozzles 218. For example, the dispensing software 210 may allow multiple medicines (or a medicine having different concentrations) to be applied separately to the porous medium simultaneously from different nozzles in a single pass, at a same time, or substantially a same time. As used herein, "single pass" may refer to one full row of drops, made by a printing head (e.g., a distance that the head travels from the extreme left position to the extreme right position during printing of each row of drops). In some embodiments, the dispensing software 210 may provide for the increased concentration of a medicine via linear additivity per a multi-pass printing process (e.g., layer-by-layer application). In embodiments, the printing device 208 may apply the medicine to the porous media horizontally or vertically, whereby when dispensing medicine, the print head moves in a horizontal motion relative to the porous media or in a vertical motion relative to the porous media.

The use of dispensing software may allow for the control of the medicine concentration by changing a saturation of the porous media with the medicine.

The dispensing software 210 may also provide for the calculation of a unit dosage volume. Given that the dot-per-inch parameter is known, and a single drop volume, the concentration may be calculated, in one or more embodiments. As a non-exhaustive example, for 70 dpi, if one inch square is filled with drops of 10 picolitre drop size, the dosage volume will be 1×70×1×70×10=49000 picolitres or 0.049 microliters. It is noted that some sources of dosing inaccuracy include, but are not limited to, aggressive effect on the applied sample after dispensing, "shedding" of the sample from the substrate after dosing, and unstable desorption of the sample from the substrate (i.e. due to the retention of the substance by the substrate during the preparing of the solution for measurement via chromatography). Embodiments may address these inaccuracies via suitable preliminary tests executed for each pharmaceutical product. For example, additives may be applied to the membrane surface to address an inaccuracy. It is also noted that embodiments may provide a cartridge or set of cartridges containing all of the substances used for the application to the membrane surface. Thus, for the production of one pharmaceutical product, the cartridges may be different depending on the local pharmaceutical regulation.

It is noted that, in one or more embodiments, the application of the medicine on the porous media and control of the printing device may be executed via desktop and mobile operating systems including, but not limited to, Windows, MacOS, Linux, Android, and iOS. One or more embodiments may provide a user interface that allows the user to control the printing device. One or more individuals or devices may execute program code of a software application for presenting and/or generating user interfaces to allow interaction with the dispensing software and/or other applications controlling the printing device 208. While FIG. 2 shows the printing device 208 including the dispensing software, processors, user interface and memory, in other embodiments, the dispensing software, processors, user interfaces and memory may be on a separate server that may be accessed by the printing device, as needed. Presentation of a user interface as described herein may comprise any degree or type of rendering, depending on the type of user interface code.

In some embodiments, the printing device 208 may have a nominal print resolution of 9600×2400 dpi, with an approximate drop volume of one picoliter. Other suitable printing device characteristics may be used. Characteristics of a printing device 208 may include, but are not limited to:

| Characteristic | Value |
| --- | --- |
| Valve dimensions ( L × W × H), mm | 86 × 17 × 52 |
| Dispensed liquids | Any liquid and viscous formulations, including polymer and oil |
| Viscosity range | 50–200,000 |
| The minimum time for a single batching, μs | 250 (one valve opening and closing) |
| Maximum single batching time | Unlimited (valve is constantly open) |
| Minimum pause time | Unlimited (valve closed) |
| Maximum dosing frequency (Hz) | 1000 at a maximum liquid temperature of 60° C. |
| Dosing accuracy (by weight) | 2% (subject to constant pressure and temperature) |
| Maximum allowable pressure, bar | 75 |
| Maximum ambient temperature, ° C. | Up to +45 |
| Maximum temperature of the dosed substance, ° C. | Up to +75 |
| Diameter of replaceable nozzles, microns | 50 to 400 |
| Number of doses before scheduled maintenance of the dispenser | 10 000 000 |
| Environmental protection class | IP54 |
| Storage temperature, ° C. | −10 to +85 |

Other characteristics of the printing device 208 may include, but are not limited to:

| Characteristic | Value |
| --- | --- |
| Print speed | 10-15 A4 sheets per minute |
| Roll printing | Possible |
| Maximum roll width | 20 cm |
| Minimum drop volume | 1p1 |
| Maximum resolution | 9600 × 1200 drops per inch |
| Printing technology | Inkjet |
| Number of colors | 5 (of which two are the same) |
| Weight | 6.6 kg |
| Height | 12.8 cm |
| Width | 45.1 cm |
| Depth | 36.8 cm |

Furthermore, the technical solution provided herein characterizes the method of using the finished pharmaceutical form for individual medicine dosing.

In accordance with the method provided herein, the medicine containing porous media is removed from the container; one fragment of the porous media the area of which corresponds to the required quantity of the medicine is detached from the membrane media, the detached fragment is placed in a container with water or water solution, the container is shaken and the content is administered perorally in the form of a solution.

The technical solution provided herein may have different embodiments. Presented below are specific embodiments of the technical solution provided herein based on the use of a jet printer.

1. A finished pharmaceutical form for individual medicine dosing is produced on the basis of water-insoluble porous media, e.g. filtering paper Grade FM (slow filtration filtering paper, used for quantitative analysis as per the GOST 12026-76 USSR Standard).

A clean rechargeable jet printer cartridge is filled, through a disposable plastic syringe with an antibacterial filter for the removal of particles of greater than 45 micrometers in size, with the preliminarily prepared solution of the medicine having the required concentration.

The charged jet printer cartridge is installed in a jet printer. The filtering paper is loaded into the jet printer paper tray. The printer is connected to a personal computer. Using any software that allows printing monotone graphic images, printing is started with said charged cartridge preinstalled, the printing quality being preset to 150 dpi.

Preliminary experiments showed that the abovementioned printing quality setting provides for the quantity of printed dots per unit area that is sufficient, with account of desorption losses, for obtaining a quantity of medicine in 50 ml of water from 1 $cm^2$ of paper area that is equal to the average therapeutic dose for the specific medicine. After application the porous media is dried and packaged.

2. A finished pharmaceutical form for individual medicine dosing is produced on the basis of water-insoluble porous media, e.g. unwoven thermally bonded cloth Grade S2.04.063008.00 (used for the filtering of milk and other food, e.g. filtering cloth made by OAO Comitex). The cloth surface is divided into identical fragments with printed separation marking lines.

A clean rechargeable jet printer cartridge is charged, through a disposable plastic syringe with an antibacterial filter for the removal of particles of greater than 45 micrometers in size, with the preliminarily prepared solution of the medicine having the required concentration.

The charged jet printer cartridge is installed in a jet printer. The unwoven cloth is loaded into the jet printer paper tray. The printer is connected to a personal computer. Using any software that allows printing monotone graphic images, printing is started with said charged cartridge pre-installed, with the printing quality being preset to 300 dpi.

Preliminary experiments showed that the abovementioned printing quality setting provides for the quantity of printed dots per unit area that is sufficient, with account of desorption losses, for obtaining a quantity of medicine in 50 ml of water from 1 cm$^2$ of paper area that is equal to the average therapeutic dose for the specific medicine.

After application the porous media is dried and packaged.

In a similar manner pharmaceutical substances are applied onto unwoven composite materials that are typically used for the fabrication of filters and packaging materials (e.g. in sachet bags). These materials may contain any types of natural or semi synthetic fibers, e.g. 67% cotton fiber+33% polyester fiber, or 60% linen fiber (L+40% semi synthetic fiber, or 80% copra fiber+20% polyester fiber etc.

3. A finished pharmaceutical form for individual medicine dosing is produced on the basis of water-insoluble porous media, e.g. fiberglass filter Grade MGB (density 140 g/m$^2$ used for the filtration of water and protein solutions, e.g. fiberglass filter made by Sartorius, USA, or Munk.tel, Germany).

A clean rechargeable jet printer cartridge Is filled, through a disposable plastic syringe with an antibacterial filter for the removal of particles of greater than 45 micrometers in size, with the preliminarily prepared solution of the medicine having the required concentration.

The charged jet printer cartridge is installed in a jet printer. The fiberglass material is loaded into the jet printer paper tray. The printer is connected to a personal computer. Using any software that allows printing monotone graphic images, printing is started with said charged cartridge pre-installed, with the printing quality being preset to 250 dpi.

After application the material is dried in air.

4. A finished pharmaceutical form for individual medicine dosing is produced on the basis of water-insoluble porous media, e.g. filtering paper Grade FM (slow filtration filtering paper, used for quantitative analysis as per the GOST 12026-76 USSR Standard).

A clean uninterrupted ink supply system consisting of 4 identical containers is charged with preliminarily prepared solutions of medicines cleaned from dust and having the required concentrations.

The charged system is installed in a jet printer. The filtering paper with perforations preliminarily made on the surface for dividing its surface into fragments of similar size is loaded into the jet printer paper tray.

The printer is connected to a personal computer. Using any software that allows printing color graphic images, printing is started with said charged cartridges preinstalled, taking into account that color images are composed by software-generated superimposition of dots from different cartridges, with the printing quality being preset to 100 dpi for the black cartridge, 150 dpi for the cyan cartridge, 200 dpi for the magenta cartridge and 250 dpi for the yellow cartridge.

Preliminary experiments showed that the abovementioned printing quality setting provides for the quantity of printed dots per unit area that is sufficient, with account of desorption losses, for obtaining a quantity of medicine in 50 ml of water from 1 cm$^2$ of paper area that is equal to the respective dose. This provides for the method embodiment wherein a jet printer is used for applying multiple pharmaceutical substances from different cartridges onto porous media.

After application the porous media is dried in air.

5. Finished pharmaceutical form as described hereinabove in p. 2 is removed from the package, and differently sized portions are cut out from the cloth along the marking lines dividing the cloth into identical fragments such as to provide the required medicine concentrations for the first and the second fragments in 50 ml of water. The detached fragments are placed into a container with water, the container is shaken and its content is stirred to achieve a homogeneous distribution of the medicine in the solution; the insoluble media is removed from the water solution as necessary, and the solution is administered perorally in the form of a solution with the required concentration.

Presented below are specific examples of the embodiment of the technical solution provided herein.

The capabilities of the technical solution provided herein will be illustrated below with the example of a device, e.g. jet printer, the software of which allows applying water or water/organic solutions in one or multiple layers onto the predetermined areas of the porous media.

As noted above, this is not the sole possible embodiment of the technical solution provided herein. For example, combinations of a programmable dosing device or a programmable nozzle with a coordination table for the placement of porous media can be used.

Preliminarily calculations allowed determining the capacity of a 0.25 cm$^2$ unit area filtering paper fragment (pure cellulose, 1000±3 mg of medicine applied, 62±2 of medicine desorbed to 30 ml of potable water) to desorb applied acetylsalicylic acid to water. The calculations showed that to obtain a pharmaceutically optimum dose of 81 mg the user should apply 130 mg of 100% acetylsalicylic acid on the unit area of said media. As the solubility of acetylsalicylic acid in water/alcohol solutions of the abovementioned concentrations is close to 100%, 50 ml of a 10% acetylsalicylic acid solution was prepared. Using a jet printer with rechargeable cartridges the solution was applied on a 236.5 cm$^2$ specimen of media made from cellulose filtering material (size 21.5*1 1 cm$^2$, format Letter) with different printing qualities in dpi and different area filling densities. This format allows applying the active pharmaceutical substance on the entire media surface without taking into account the non-printable margins typically formed at the edges of an A4 format sheet. Following that the quantity of acetylsalicylic acid applied per unit area was analyzed depending on software controlled printing quality (in dpi). Using the specially plotted graduation curve the required printing densities in dpi were selected for applying 130 mg per 0.25 cm$^2$, or 520 mg/cm$^2$. The specimen was dried in a hot air flow for guaranteed removal of the water/alcohol solvent and packaged in a polymer container protecting the specimen from direct sunlight. Then the specimen was removed from the container and placed in a glass with water.

After desorption of adsorbed acetylsalicylic acid to the water the medicine is ready for use.

A similar procedure was conducted for d, 1-2-(4-isobutylphenyl)-propionic acid (the active pharmaceutical substance of the Ibuprofen medicine) and a fiberglass membrane made by Algstrem, USA, used in immunology. The experiments showed that the possible quantity of d, 1-2-(4-isobutylphenyl)-propionic acid that can be applied on 1 cm$^2$ (unit area) of the abovementioned specimen is 300±2 mg, of which 246±2 was desorbed to 50 ml of potable water, i.e. 82%.

Taking into account that the typical dose of d, 1-2-(4-isobutylphenyl)-propionic acid in an Ibuprofen pill is 200 mg, the finished pharmaceutical form provided as above is capable of providing the typical dosage from unit area. For coloring the medicine solution, E162f (licopin) coloring agent was added to the solution which is approved for food industry in the Russian Federation and abroad (FDA/CFSAN Food Color Facts). After application and drying the finished pharmaceutical form had a reddish hue. The application and administration procedures for Ibuprofen are similar to the preparation and administration procedures for the abovementioned acetylsalicylic acid pharmaceutical form.

A similar procedure was conducted for Ampicillin antibiotic and water soluble alginate paper. A single Ampicillin dosage for adult administration is a 250-500 mg pill with an administration regimen of 3-4 times daily. For children with a body weight of below 20 kg the administration regimen is 12.5-25 mg/kg every 6 h. It has been determined that the quantity of the medicine that can be applied on 1 cm$^2$ (unit area specimen) at a time with a jet printer is 100 mg. Before application the medicine solution was colored with yellow coloring agent lutein (E161b). Simultaneously with the application of the active substance, technical notes and separation marking lines were printed from another cartridge in black (E153 coal food coloring). After application and drying the color of the finished pharmaceutical form was bright yellow with black marking and technical notes. The application and administration procedures for Ampicillin are similar to the preparation and administration procedures for the abovementioned acetylsalicylic acid pharmaceutical form.

Thus, without changing the preparation of the required finished pharmaceutical form a patient can separate an area of the media containing the required dosage of the antibiotic depending on the patient's weight and the doctor's order.

The above examples do not limit the applications of the finished pharmaceutical form provided herein.

One unconventional task that can be solved with the finished pharmaceutical form provided herein is local production of pharmaceutical forms taking into account potential applicable confessional aspects. Currently, questions arise in a number of Islamic states regarding the necessity of the Halal certification of pharmaceutical products because large international pharmaceutical companies often refuse to disclose the composition of auxiliary components they use for the production of finished pharmaceutical forms. The finished pharmaceutical form with individual medicine dosing capability provided herein can be produced locally in order to accommodate for any applicable requirements imposed upon pharmaceutical raw materials, components and their quality thus allowing for the establishment of pharmaceutical production facilities compliant with the Halal requirements.

One more potential application of this invention is the revival of compounding pharmacies so the doctor at the office can issue an electronic peroral pharmaceutical form order for a patient, such order to contain the name of the required pharmaceutical substance or preparation and the required dosage and administration regimen, following which the patient having paid for the order can receive the finished pharmaceutical form in accordance with this invention, containing printed administration regimen information and single dose fragment separation marking lines.

As described above, non-exhaustive examples of medicines include vitamins, antibiotics, dietary supplements, fortified products, premixes, antivirals, medicines, anti-inflammatory drugs, metabolites, anti-tumor oral drugs, diagnostical contrast oral substances, nootripics, medical psychotherapeutic drugs (e.g., THC, CBD, other cannabis extracts).

Fullerenol S60 (OH) 42, which has an adsorbing, detoxifying and antidiarrheal effect. Fullerenol is believed to absorb pathogenic strains and their toxins in infectious diseases such as acute dysentery, salmonellosis, viral hepatitis, typhoid fever, leptospirosis, hemorrhagic fevers, psittacosis, etc. By binding toxins of microbial and endogenous origin, the drug reduces the load on the organs of detoxification and excretion and eliminates diarrhea in acute intestinal diseases (rotavirus gastroenteritis, cholera, staphylococcal enterotoxin poisoning). Fullerenol S60 (OH) 42 includes other properties and provides other benefits.

Pyridoxine (vitamin B6), which is involved in the metabolism and is essential for the normal functioning of the central and peripheral nervous system. Entering the body, it is phosphorylated, converted into pyridoxal-5-phosphoate and is part of the enzymes that decarboxylate and transaminate amino acids. Pyridoxine participates int eh exchange of tryptophan, methionine, cysteine, glutamic and other amino acids. Pyridoxine plays an important role in the exchange of histamine, and promotes the normalization of lipid metabolism. Pyridoxine includes other properties and provides other benefits.

Vitamin C, which participates in the regulation of oxidation-reduction processes, carbohydrate metabolism, blood clotting, tissue regeneration, increases the body's resistance to infections, reduces vascular permeability, reduces the need for vitamins B1, B2, A, E, folic acid and pantothenic acid. Vitamin C regulates immunological reactions, promotes phagocytosis, and inhibits the release and accelerates the degradation of histamine, as well as, inhibits the formation of Pg and other mediators of inflammation and allergic reactions. Vitamin C includes other properties and provides other benefits.

Nicotinamide (Vitamin B3, Vitamin PP), which is an important component in NAD and NADP, and is involved in oxidation-reduction processes in the cell. It participates int eh metabolism of fats, proteins, amino acids, purines, tissue respiration and glycogenolysis. Nicotinamide includes other properties and provides other benefits.

Tetracycline, which is a bacteriostatic antibiotic from the tetracyclines group. Tetracycline violates the formation of a complex between the transport RNA and the ribosome, which leads to suppression of protein synthesis. Tetracycline is active against gram-positive microorganisms (e.g., *Staphylococcus* spp, *Streptococcus, Bacillus anthracis*, etc.). Tetracycline includes other properties and provides other benefits. The above examples illustrate the feasibility of the technical result claimed herein in different embodiments of the technical solution provided herein.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Aspects from the various embodiments described, as well as other known equivalents for each such aspects, can be mixed and matched by one of ordinary skill in the art to construct additional embodiments and techniques in accordance with principles of this application.

Those in the art will appreciate that various adaptations and modifications of the above-described embodiments can be configured without departing from the scope and spirit of the claims. Therefore, it is to be understood that the claims may be practiced other than as specifically described herein.

The invention claimed is:

1. A method comprising:
   receiving a first quantity of at least one medicine in at least one cartridge of a plurality of cartridges of a printing device;
   receiving a porous media in the printing device;
   dispensing a first drop of the at least one medicine onto the porous media;
   applying a first individual coloring agent onto the porous media, the dispensed drop of the at least one medicine and the first individual coloring agent presenting as a specific color on the porous media; and
   drying the dispensed drop on the porous media.

2. The method of claim 1, wherein the printing device is an inkjet printer.

3. The method of claim 2, further comprising:
   executing a flushing process prior to receipt of the first quantity of the at least one medicine.

4. The method of claim 3, wherein the flushing process further comprises:
   receiving a quantity of washing medium into a plurality of head nozzles of a print head of the printing device;
   receiving a second quantity of washing medium into one or more cartridges;
   coupling the one or more cartridges to the print head;
   executing a test print;
   determining whether the plurality of head nozzles and the one or more cartridges are clean; and
   in a case that at least one of the one or more cartridges and at least one of the plurality of head nozzles is not clean, receiving a second quantity of washing medium into the one or more cartridges and the plurality of head nozzles.

5. The method of claim 1, wherein the porous media is an edible paper.

6. The method of claim 1, wherein the medicine is one of a vitamin, an antibiotic, an antiviral substance and a dietary supplement.

7. The method of claim 1, further comprising:
   dispensing a second drop of the first medicine on the porous media, wherein the first drop is separated from the second drop on the porous media by a separation marking line on the porous media.

8. The method of claim 1, further comprising:
   receiving a first quantity of a second medicine in a second cartridge of the plurality of cartridges; and
   dispensing at least one drop of the second medicine on the porous media.

9. The method of claim 8, wherein the first medicine and the second medicine are dispensed at a same time.

10. The method of claim 8, wherein the dispensed drop of the first medicine and the dispensed drop of the second medicine are spaced apart on the porous media by a pre-set amount.

11. The method of claim 1, further comprising:
    dispensing a second drop of the first medicine on the porous media, wherein the second drop is a different concentration than the first drop.

12. The method of claim 11, wherein each of the first drop and the second drop includes a different individual coloring agent having a specific color, wherein the specific color is displayed on the porous media.

13. The method of claim 1, wherein the first drop is one of: 1. a first dose and 2. a part of a first dose.

14. The method of claim 2 wherein the inkjet printer includes a piezoelectric element, and a quantity of the first medicine dispensed on the porous media is controlled by controlling an amount of time the piezoelectric element is open, limiting an application time of medicines having the same concentration.

15. The method of claim 1, wherein the porous media receives the dispensed first drop in a skin mask shape on the porous media.

16. The method of claim 15, wherein the porous media includes more than one skin mask shape.

* * * * *